US00PP11727P

United States Patent [19]

Cain

[11] Patent Number: Plant 11,727

[45] Date of Patent: Dec. 26, 2000

[54] GRAPE PLANT NAMED 'SUGRAFIFTEEN'

[75] Inventor: David Cain, Bakersfield, Calif.

[73] Assignee: Sun World International Inc., Bakersfield, Calif.

[21] Appl. No.: 09/197,198

[22] Filed: Nov. 20, 1998

[51] Int. Cl.[7] ..... A01H 5/00

[52] U.S. Cl. ..... Plt./207

[58] Field of Search ..... Plt./207

[56] References Cited

U.S. PATENT DOCUMENTS

P.P. 3,106 4/1972 Garabedian ..... Plt./207

P.P. 4,784 11/1981 Olmo et al. ..... Plt./207

P.P. 4,788 11/1981 Olmo et al. ..... Plt./207

P.P. 6,464 12/1988 Karniel ..... Plt./207

*Primary Examiner*—Howard J. Locker

*Assistant Examiner*—Melissa L. Kimball

*Attorney, Agent, or Firm*—Knobbe, Martens, Olson & Bear LLP

[57] ABSTRACT

A new distinct variety of grapevine producing extremely firm, yellow-green, round to obovate berries which are tenaciously attached to a strong and well lignified rachis.

1 Drawing Sheet

BACKGROUND AND SUMMARY OF THE INVENTION

This invention relates to the discovery and asexual propagation of a new variety of grapevine, *Vitis vinifera* cv. 'Sugrafifteen'. The new variety was first created in May, 1988 by David W. Cain near Wasco, Kern County, Calif., the variety being originated by a controlled cross. The new variety is characterized by its extremely firm, yellow-green, round to obovate berries which are tenaciously attached to a strong and well lignified rachis.

The seed parent of the new variety is the 'Dawn Seedless' variety (U.S. Plant Pat. No. 4,788). The pollen parent is the 'Flame Seedless' variety (unpatented). The parent varieties were first crossed in May, 1988, and first flowering of the new variety was in May, 1990. The new variety was first asexually propagated by David W. Cain in 1990 in Wasco, Kern County, Calif., using hardwood cuttings.

The new grapevine variety cv. 'Sugrafifteen' most nearly resembles its parent varieties, the 'Flame Seedless' and 'Dawn Seedless' varieties. It differs from the 'Flame Seedless' variety by producing fruits of a yellow-green color in contrast to the red coloration of 'Flame Seedless'. It differs from the 'Dawn Seedless' and 'Perlette' (unpatented) varieties by possessing larger, much firmer, more uniform berries that are later ripening and that are more responsive to gibberellic acid treatments. Berries of the new variety become more yellow in color as they mature than berries of the 'Dawn Seedless' variety. The new variety also has a much more highly lignified, stronger rachis structure with a more well matured woody peduncle than the 'Dawn Seedless'.

The new variety differs from the 'Sugraone' variety (U.S. Plant Pat. No. 3,106) by producing later ripening berries that are much more uniform in size, more yellow in color, and firmer. They also exhibit less phytotoxic effects from, and are more responsive to, gibberellic acid applications than 'Sugraone'. The vine of the new variety is less vigorous than the 'Sugraone' and exhibits much less axillary branching than 'Sugraone'. It is extremely productive and may be pruned to two bud spurs.

The new variety differs from other commonly grown white seedless grapes such as the 'Thompson Seedless' (unpatented), 'Centennial Seedless' (U.S. Plant Pat. No. 4,784) and 'King Husany' (U.S. Plant Pat. No. 6,464) varieties, by possessing much less elongated and more nearly round berries of much firmer flesh texture, which have much stronger attachment to the rachis.

The new 'Sugrafifteen' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
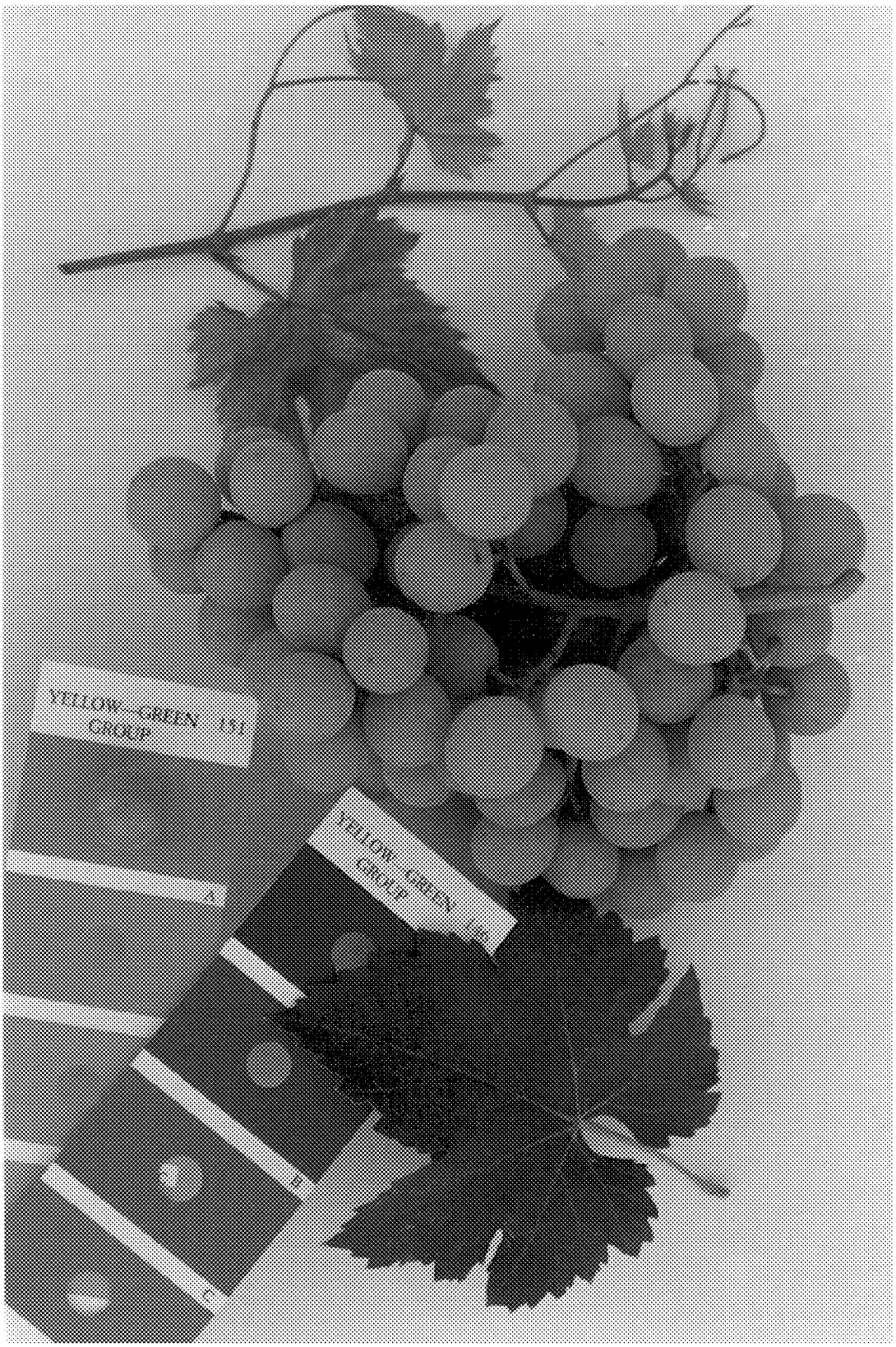

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrafifteen' plants grown in the vicinity of Wasco, Kern County, Calif., during 1998 (or 1994 where indicated), and is believed to apply to plants of the variety grown under similar conditions of soil and climate elsewhere:

VINE

General:

*Size.*—Small.

*Vigor.*—Medium.

*Density of foliage.*—Medium.

*Productivity.*—Very productive up to 28.2 kg/vine.

*Root stock.*—Own root.

Trunk:
*Shape*.—Slender.
*Straps*.—Short, split, very narrow.
*Surface texture*.—Medium shaggy.
*Inner bark color*.—About Greyed-Orange 176D.

SHOOTS

Young shoot:
*Form of tip*.—Half-open.
*Distribution of anthocyanin coloration of tip*.—Absent.
*Intensity of anthocyanin coloration of tip*.—Absent or very weak.
*Density of prostrate hairs on tip*.—Sparse.
*Erect hairs on tip*.—Absent.
Flowering shoot:
*Vigor during flowering*.—Medium.
*Attitude during flowering on shoots which are not tied*.—Erect.
*Color of dorsal side of internodes*.—About Yellow-Green 145A.
*Color of ventral side of internodes*.—About Yellow-Green 145A.
*Color of dorsal side of nodes*.—About Yellow-Green 145A.
*Color of ventral side of nodes*.—About Yellow-Green 145A.
*Erect hairs on nodes*.—None.
*Erect hairs on internode*.—Absent.
*Prostrate hairs on nodes*.—None.
*Prostrate hairs on internodes*.—Absent.
*Anthocyanin coloration of buds*.—Absent.
Tendrils:
*Distribution on the shoot at full flowering*.—Discontinuous.
*Thickness*.—Medium.
*Color*.—About Yellow-Green 144A.
*Form*.—Trifurcated.
*Number of consecutive tendrils*.—Up to two.
*Length of tendril*.—Long, about 26.9 cm.

LEAVES

Young leaves:
*Color of upper surface of first 4 distral unfolded leaves*.—About Yellow-Green 144A.
*Average intensity of anthocyanin coloration of six distal leaves prior to flowering*. —Absent.
*Density of prostrate hairs between veins at lower surface of 4th distal unfolded leaf*.—Absent or very sparse.
*Density of erect hairs between veins at lower surface of 4th distal unfolded leaf*.—Absent or very sparse.
*Density of prostrate hairs on veins at lower surface of 4th distal unfolded leaf*.—Sparse.
*Density of erect hairs on veins at lower surface of 4th distal unfolded leaf*.—Absent or very sparse.
Mature leaves:
*Average length*.—About 15.9 cm.
*Average width*.—About 19.8 cm.
*Size of blade*. Large.
*Shape of blade*.—Pentagonal.
*Number of lobes*.—5.
*Anthocyanin coloration of main veins on the upper side of the blade*.—Absent.
*Mature leaf profile*.—Involute.
*Blistering surface of blade upper surface*.—Weak.
*Leaf blade tip*.—In the plane of the leaf.
*Undulation of margin*.—Pronounced.
*Apex*.—Cuspidate.
*Thickness*.—Thin.
*Undulation of blade between main and lateral veins*.—Absent.
*Shape of teeth*.—Both sides straight.
*Length of teeth*.—Medium.
*Ratio length/width of teeth*.—Small.
*General shape of petiole sinus*.—Slightly open.
*Tooth at petiole sinus*.—Absent.
*Petiole sinus limited by veins*.—Absent.
*Shape of upper lateral sinus*.—Open.
*Depth of upper lateral sinus*.—Shallow.
*Shape of lower lateral sinus*.—Open.
*Depth of lower lateral sinus*.—Medium.
*Prostrate hairs between veins on lower surface of blade*.—Absent.
*Erect hairs between veins on lower surface of blade*.—Absent.
*Prostrate hairs on main veins on lower surface of blade*.—None.
*Erect hairs on main veins on lower surface of blade*.—None.
*Prostrate hairs on main veins on upper surface of blade*.—Absent.
*Autumm coloration of leaves*.—About Yellow 11A.
Upper surface:
*Color*.—About Green 141B.
*Surface texture*.—Rugose.
*Surface appearance*.—Semi-glossy.
*Goffering of blade*.—Present.
Lower surface:
*Color*.—About Green 143A.
*Anthocyanin coloration of main veins on lower leaf surface*.—Absent.
*Glossiness*.—Strong.
*Pubescence*.—Absent.
*Surface texture*.—Smooth.
*Surface appearance*.—Semi-glossy.
Petiole:
*Length of petiole*.—Long, about 14.7 cm.
*Length of petiole compared to middle vein*.—Slightly shorter.
*Prostrate hairs on petiole*.—None.
*Erect hairs on petiole*.—None.
*Shape of base of petiole sinus*.—V-shaped.
Woody shoot:
*Shape*.—Stocky.
*Internode length*.—Short to medium, about 10.6 mm.
*Width at node*.—About 13.5 mm.
*Cross section*.—Circular.
*Surface*.—Ribbed.
*Main color*.—About Greyed-Orange 166D.
*Lenticels*.—Inconspicuous.
*Density of erect hairs on nodes*.—None or very sparse.
*Density of erect hairs on internodes*.—None or very sparse.
*Growth of axillary shoots*.—Weak, about 21.6 cm.
*Maturation of canes*.—Canes become highly lignified and woody quite early.
Buds:
*Shape*.—Pointed.
*Size*.—Large, about 7.8 ×6.6 mm (length×width).

*Position*.—Slightly held out, about 45° angle.
*Cane bud fruitfulness*.—Basal most fruitful; medium and distal fruitful.
*Time of bud burst*.—Medium.

Fowers

General:
*Flower sex*.—Perfect.
*Length of first inflorescence*.—Long, about 22.6 cm.
*Position of first flowering node*.—5th node (current season growth).
*Number of inflorescences per shoot*.—1.1 to 2.
*Date of full bloom*.—May 23, 1998.
*Time of bloom*.—Medium, as compared with similar varieties in the growing area of Wasco, Kern County, Calif.
*Duration of bloom period*.—Average, approximately 10 days.
*Size* (*diameter of fully open flower*).—Medium.
*Color*.—About Yellow-Green 145B.

FRUIT

General:
*Ripening period*.—Medium, about with the 'Thompson Seedless' variety.
*Date of ripening*.—August 1, varying from July 15 to August 20, depending upon the year.
*Use*.—Fresh market.
*Keeping quality*.—Medium.
*Resistance*.—Insects: Typical of *Vitis vinifera*. Diseases: Typical of *Vitis vinifera*.
*Shipping quality*.—Good.
*Date of first harvest*.—Aug. 20, 1998.
*Solids-sugar*.—High (~21%).
*Refractometer test*.—About 23° brix on Oct. 29, 1998.
*Acid*.—Low.
*Juice pH*.—3.9.

Cluster:
*Bunch size* (*penduncle excluded*).—Medium.
*Bunch length* (*peduncle excluded*).—Intermediate to long, about 21.1 cm.
*Bunch width*.—About 16.9 cm.
*Bunch weight*.—High, about 807 g (average).
*Bunch density*.—Dense.
*Number of berries*.—About 164.
*Form*.—Circular.

Peduncle:
*Length of peduncle*.—Medium, about 5.8 cm.
*Lignification of peduncle*.—Strong.
*Color*.—About Yellow-Green 144A.

Berry:
*Size*.—Medium.
*Uniformity of size*.—Very uniform under a wide range of environments.
*Berry weight*.—Medium, natural weight averages 3.7 to 4.1 g; can attain an average of 7.0 to 7.6 g when plant is girdled and treated with gibberellic acid.
*Shape*.—Round to slightly obovate.
*Presence of seeds*.—Rudimentary, about 7.4 mg/seed fresh weight.
*Cross section*.—Circular.
*Dimensions*.—(1994 data) longitudinal axis about 21.3 mm; horizontal axis about 19.1 mm.
*Skin color* (*without bloom*).—About Yellow-Green 151A.
*Anthocyanin coloration of flesh*.—Translucent, not colored.
*Juiciness of flesh*.—Very slightly juicy.
*Berry firmness*.—Extremely firm.
*Particular flavor*. —Neutral to faint apple flavor.
*Bloom* (*cuticular wax*).—Strong.
*Pedicel length*.—Intermediate, about 6.6 mm.
*Berry separation from pedicel*.—Very difficult.
*Visibility of hilum*.—Very clear.
*Torus*.—Medium thick.

Skin:
*Thickness*.—Medium.
*Texture*.—Medium.
*Reticulation*.—Absent.
*Roughness*.—Present, slightly ridging especially near the stylar end.
*Tenacity*.—Tenacious to flesh.
*Tendency to crack*.—Highly resistant.

What is claimed is:

1. A new and distinct variety of grapevine cv. 'Sugrafifteen' as herein illustrated and described.

* * * * *